US008681217B2

(12) United States Patent
Hori

(10) Patent No.: US 8,681,217 B2
(45) Date of Patent: Mar. 25, 2014

(54) INSPECTION APPARATUS AND MEASUREMENT METHOD

(75) Inventor: Fumio Hori, Tokyo (JP)

(73) Assignee: Olympus Corporation, Tokyo (JP)

( * ) Notice: Subject to any disclaimer, the term of this patent is extended or adjusted under 35 U.S.C. 154(b) by 385 days.

(21) Appl. No.: 12/840,551

(22) Filed: Jul. 21, 2010

(65) Prior Publication Data

US 2012/0019653 A1    Jan. 26, 2012

(51) Int. Cl.
*H04N 7/18*    (2006.01)

(52) U.S. Cl.
USPC .......................................... 348/136; 348/135

(58) Field of Classification Search
USPC ................................................... 348/88–160
See application file for complete search history.

(56) References Cited

U.S. PATENT DOCUMENTS

| | | | |
|---|---|---|---|
| 4,980,763 A | 12/1990 | Lia | |
| 5,070,401 A | 12/1991 | Salvati et al. | |
| 7,113,651 B2 * | 9/2006 | Liang | 382/284 |
| 2004/0246495 A1 * | 12/2004 | Abe | 356/603 |
| 2008/0030597 A1 * | 2/2008 | Olsen et al. | 348/227.1 |
| 2009/0225320 A1 | 9/2009 | Bendall et al. | |
| 2009/0225321 A1 | 9/2009 | Bendall et al. | |
| 2009/0225329 A1 | 9/2009 | Bendall et al. | |
| 2009/0225333 A1 * | 9/2009 | Bendall et al. | 356/626 |

FOREIGN PATENT DOCUMENTS

| | | |
|---|---|---|
| CN | 101556143 A | 10/2009 |
| JP | 05-280945 | 10/1993 |
| JP | 2002-257528 | 9/2002 |
| JP | 2003-014426 | 1/2003 |
| JP | 3475245 | 12/2003 |
| JP | 2009-150773 | 7/2009 |
| JP | 2009-180689 | 8/2009 |

* cited by examiner

*Primary Examiner* — Andy Rao

(74) *Attorney, Agent, or Firm* — Scully, Scott, Murphy & Presser, P.C.

(57) ABSTRACT

An inspection apparatus including: an insertion portion which is inserted into a device under inspection; a projection unit which projects light which forms a striped pattern onto an object inside the device, the striped pattern includes a plurality of linear patterns used to measures the object by a phase shift method; an imaging unit which is provided in the insertion portion and images the object onto which the striped pattern is projected and generates image data; a generation unit which generates first image data forming a first image not including the striped pattern and second image data forming a second image including the striped pattern from the image data generated by the imaging unit; a designation unit which designates a position in the first image based on an instruction input through an input device; a display unit which displays the first image and the second image and displays a mark at the position in the first image designated by the designation unit; and a measurement unit which measures the object using the second image data with the phase shift method based on the position indicated by the mark.

6 Claims, 14 Drawing Sheets

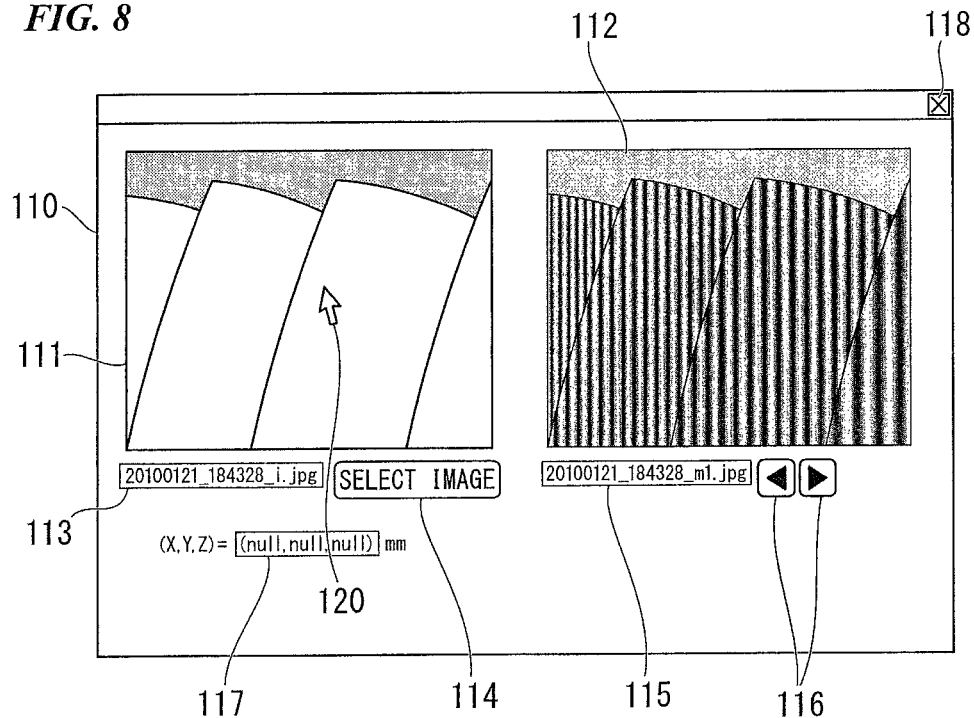
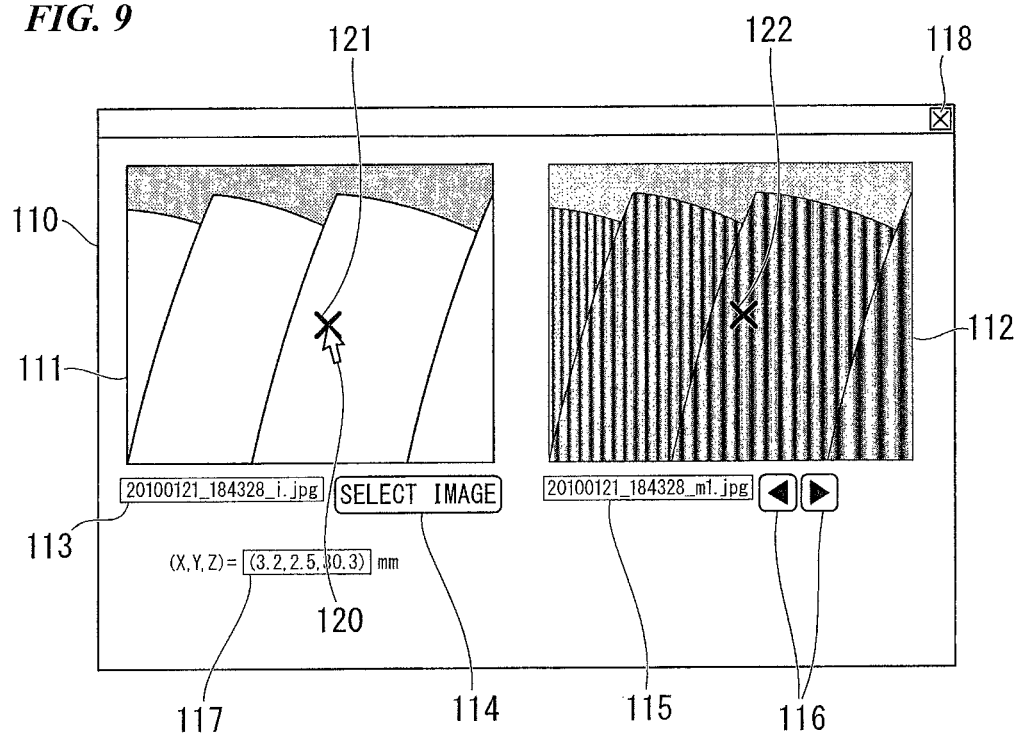

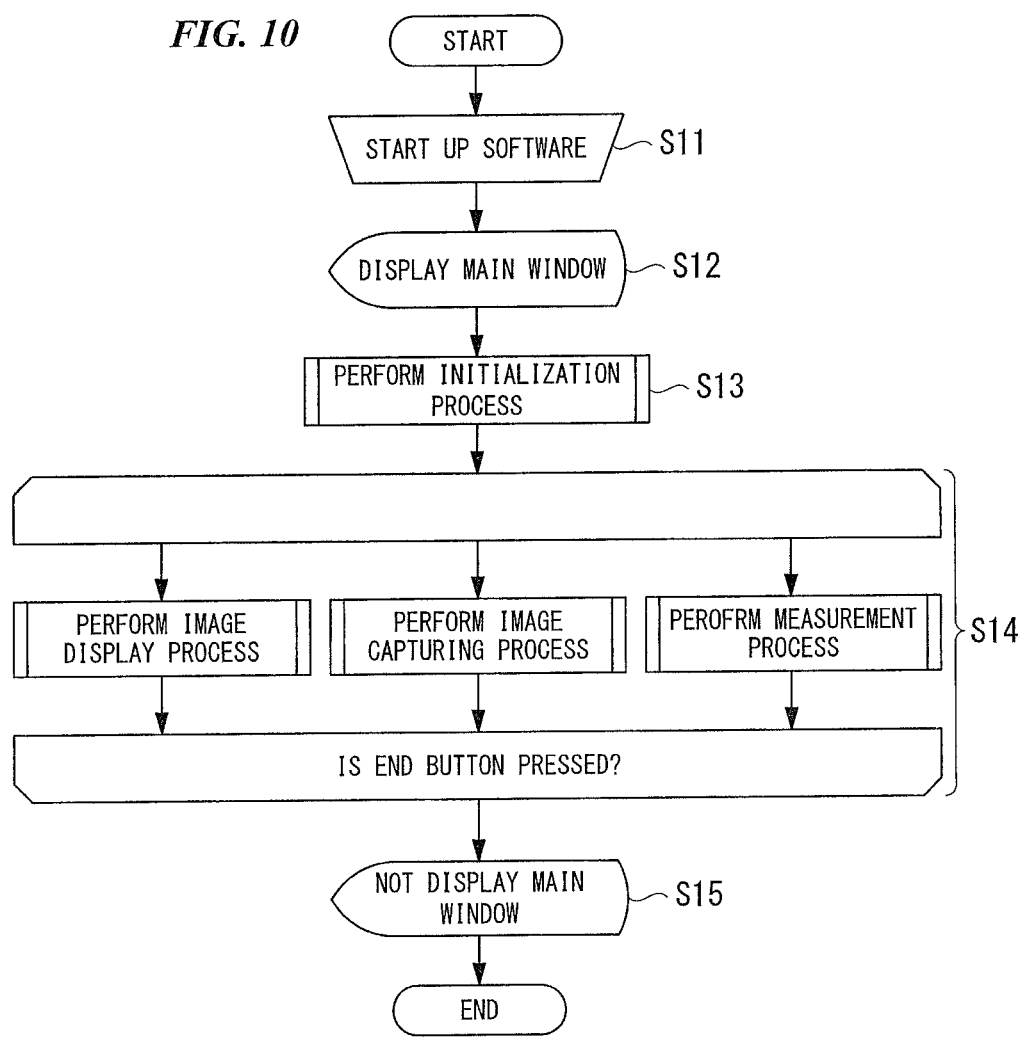
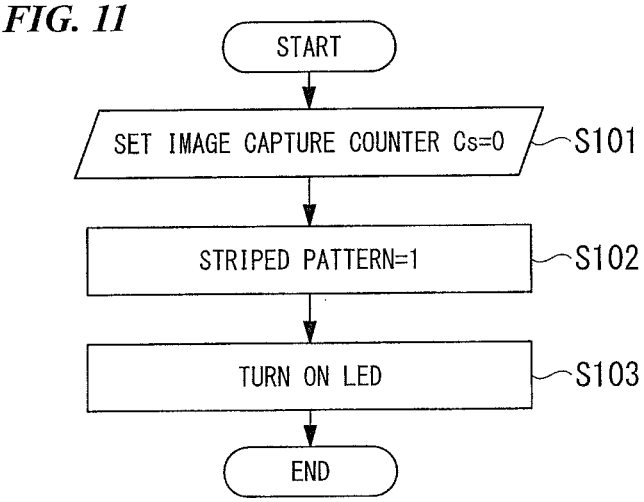

702

INSPECTION APPARATUS AND MEASUREMENT METHOD

BACKGROUND OF THE INVENTION

1. Field of the Invention

The present invention relates to an inspection apparatus measuring an object based on image data acquired by imaging an object and a measurement method.

2. Description of Related Art

Industrial endoscope apparatuses are used for observation or inspection of internal damage or corrosion of boilers, turbines, engines, pipes, and the like. An endoscopic apparatus having functions of projecting a striped pattern onto an object, capturing object image including the striped pattern with an endoscope, and measuring an object using a phase shift method is known.

US Patent Publication No. 2009/0225333 discloses an endoscope apparatus measuring an object using the above-mentioned phase shift method.

SUMMARY OF THE INVENTION

According to an aspect of the invention, there is provided an inspection apparatus including: an insertion portion which is inserted into a device under inspection; a projection unit which projects light which forms a striped pattern onto an object inside the device, the striped pattern includes a plurality of linear patterns used to measures the object by a phase shift method; an imaging unit which is provided in the insertion portion and images the object onto which the striped pattern is projected and generates image data; a generation unit which generates first image data forming a first image not including the striped pattern and second image data forming a second image including the striped pattern from the image data generated by the imaging unit; a designation unit which designates a position in the first image based on an instruction input through an input device; a display unit which displays the first image and the second image and displays a mark at the position in the first image designated by the designation unit; and a measurement unit which measures the object using the second image data with the phase shift method based on the position indicated by the mark.

BRIEF DESCRIPTION OF THE DRAWINGS

FIG. 8 is a diagram schematically illustrating a measurement window displayed on the monitor according to the first embodiment of the invention.

FIG. 9 is a diagram schematically illustrating the measurement window displayed on the monitor according to the first embodiment of the invention.

FIG. 10 is a flowchart illustrating a flow of operations of the inspection apparatus according to the first embodiment of the invention.

FIG. 11 is a flowchart illustrating a flow of an initialization process according to the first embodiment of the invention.

DETAILED DESCRIPTION OF THE PREFERRED EMBODIMENTS

First Embodiment

Figure 1:
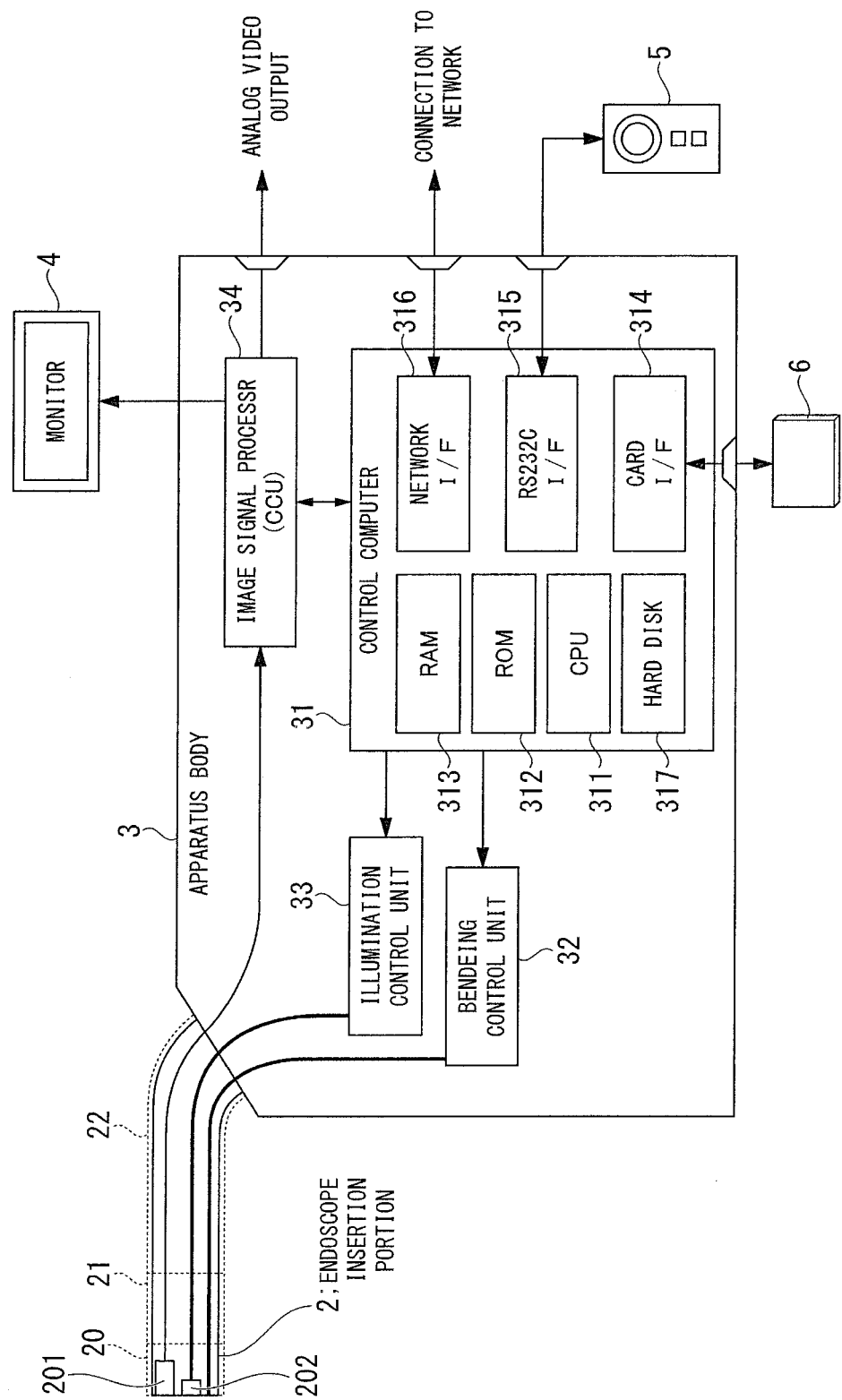
FIG. 1 is a diagram schematically illustrating a configuration of an inspection apparatus according to a first embodiment of the invention.

Hereinafter, a first embodiment of the invention will be described with reference to the accompanying drawings. FIG. 1 shows the configuration of an inspection apparatus according to the first embodiment of the invention. As shown in FIG. 1, the inspection apparatus 1 includes an endoscope insertion portion 2 and an apparatus body 3 connected to the endoscope insertion portion 2.

The endoscope insertion portion 2 includes a distal end portion 20 formed of a hard material and a bending portion 21 which can be bended in all directions, and a flexible tube portion 22 having flexibility, which are sequentially connected from the distal end. An imaging unit 201 and a lamp unit 202 are disposed in the distal end portion 20. The detailed configuration of the distal end portion 20 will be described later.

A control computer 31, a bending control unit 32, an illumination control unit 33, and an image signal processor 34 (CCU) are disposed in the apparatus body 3.

The control computer 31 includes a CPU 311, a ROM 312, a RAM 313, a card I/F 314 (card interface), an RS-232C I/F 315 (RS-232C interface), a network I/F 316 (network interface), and a hard disk 317.

The CPU 311 controls the units of the inspection apparatus 1 to perform processes suitable for purposes and controls the overall operation of the inspection apparatus 1, by executing programs stored in the ROM 312. The RAM 313 used as a work area for temporarily storing data by the CPU 311.

An operation unit 5 giving an operation instruction to the inspection apparatus 1 is connected to the RS-232C I/F 315. When a user operates the operation unit 5, communications necessary for controlling the operations of the inspection apparatus 1 are performed based on the operated details.

A memory card 6 can be freely mounted on and demounted from the card I/F 314. By mounting the memory card 6 on the card I/F 314, control process information or image information stored in the memory card 6 can be input or data such as the control process information of the image information can be recorded in the memory card 6, under the control of the CPU 311.

The network I/F 316 is an interface connecting the inspection apparatus 1 to another apparatus via a communicable network. Accordingly, for example, image data and the like can be transmitted to an external personal computer.

The hard disk 317 stores various data.

The bending control unit 32 is connected to the bending portion 21 of the endoscope insertion portion 2 and bends the bending portion 21. Accordingly, the distal end portion 20 can be moved in all directions.

The illumination control unit 33 is connected to the illumination unit 202 built in the distal end portion 20 and controls the illumination unit 202. Specifically, the illumination control unit 33 controls the ON and OFF states of a visible light LED (Light Emitter Diode) or an ultraviolet light LED of the illumination unit 202 or the pattern switching of a pattern filter of the illumination unit 202.

The image signal processor 34 composes a graphic image signal, inspection image data, and measurement image data which are generated under the control of the CPU 311 so as to display a main window or a measurement window, and outputs the composed image to a monitor 4 or an external terminal. The image signal processor 34 can also perform a process for independently displaying an image such as an endoscope image (inspection image, measurement image, or the like) or an operation menu. Accordingly, the main window, the measurement window, the inspection image, the operation menu image, or the like are displayed on the screen of the monitor 4.

Figure 2:
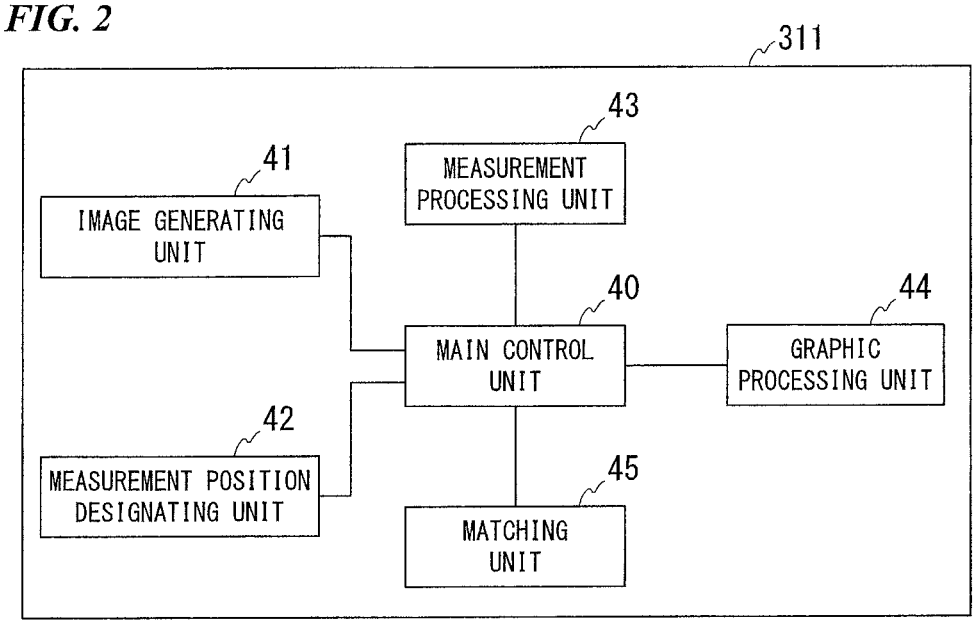
FIG. 2 is a block diagram illustrating the functional configuration of a CPU according to the first embodiment of the invention.

Then, the functional configuration of the CPU 311 will be described. FIG. 2 is a block diagram illustrating the functional configuration of the CPU 311 according to this embodiment. In the shown example, the CPU 311 serves as a main control unit 40, an image generating unit 41, a measurement position designating unit 42, a measurement processing unit 43, a graphic processing unit 44, and a matching unit 45.

The main control unit 40 controls the allocation of processes to the image generating unit 41, the measurement position designating unit 42, the measurement processing unit 43, the graphic processing unit 44, and the matching unit 45, and controls the overall operations of the inspection apparatus 1.

The image generating unit 41 generates the inspection image data used in displaying an image and the measurement image data used in a measurement process based on an image signal supplied from the imaging unit 201 disposed in the distal end portion 20 of the endoscope insertion portion 2. The measurement position designating unit 42 designates a position to be measured in an image displayed on the monitor 4 based on a user's operation result using the operation unit 5. A mark is put at the position to be measured. The measurement processing unit 43 performs a process of calculating three-dimensional coordinates or a measurement process of measuring the length or area of an object based on a phase shift method using the plural measurement image data onto which a striped pattern including plural linear patterns is projected. The graphic processing unit 44 generates a graphic image signal for displaying a variety of information displayed as texts or numerical values on a display screen, a cursor, and the like. The matching unit 45 performs a matching process of calculating a position of a corresponding point in the measurement image corresponding to the mark position indicating the measurement position in the inspection image designated by the measurement position designating unit 42.

Figure 3:
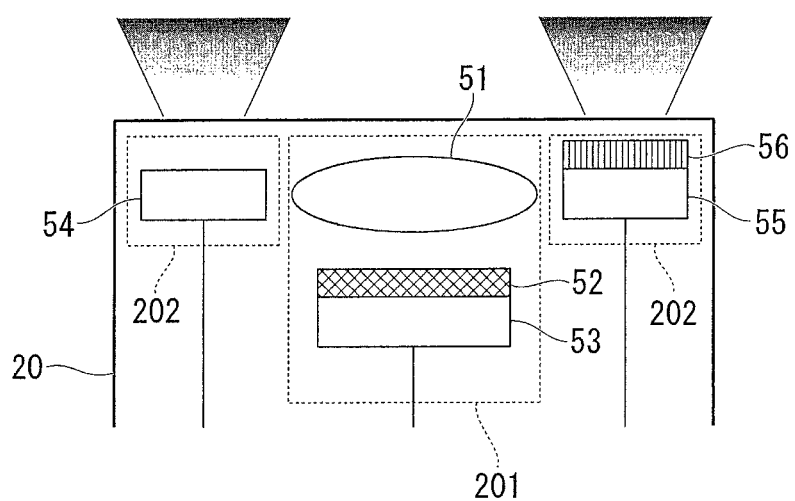
FIG. 3 is a diagram schematically illustrating the configuration of a distal end portion according to the first embodiment of the invention.

The configuration of the distal end portion 20 will be described. FIG. 3 is a diagram schematically illustrating the configuration of the distal end portion 20 according to this embodiment. In the shown example, the imaging unit 201 and the illumination unit 202 are disposed in the distal end portion 20. The imaging unit 201 includes an imaging optical system 51, a color filter 52, and an imaging device 53. The color filter 52 is disposed on the light-receiving surface of the imaging device 53. The imaging optical system 51 forms an object image on the light-receiving surface of the imaging device 53. The color filter 52 is a filter transmitting only light in a specific wavelength band. The imaging device 53 photoelectrically converting the object image formed by the imaging optical system 51 and the color filter 52 to generate an image signal. The configuration of the color filter 52 will be described later.

The illumination unit 202 includes a visible light LED 54, an ultraviolet light LED 55, and a pattern filter 56. Alternatively, lamps, a laser diode (LD) or the like can be adapted instead of the LEDs in this or another embodiment. The visible light LED 54 emits visible light to be applied to the object. The ultraviolet light LED 55 emits ultraviolet light to be applied to the object. The pattern filter 56 is a filter blocking the ultraviolet light emitted from the ultraviolet light LED 55 in a striped pattern and is disposed on the ultraviolet light-emitting surface of the ultraviolet light LED 55. Accordingly, the ultraviolet light emitted from the ultraviolet light LED 55 projects a striped pattern onto the object through the pattern filter 56.

The pattern filter 56 switches its pattern among striped pattern "1", striped pattern "2", and striped pattern "3" under the control of the illumination control unit 33. Striped patterns "1" to "3" partially block the ultraviolet light emitted from the ultraviolet light LED 55 and include plural linear patterns having different phases. By switching the striped patterns, it is possible to project striped patterns having different phases onto the object.

Figure 4:
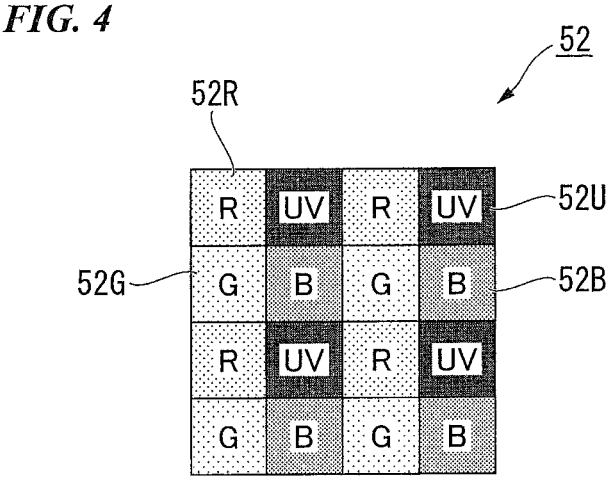
FIG. 4 is a diagram schematically illustrating an arrangement of color filters according to the first embodiment of the invention.

The configuration of the color filter 52 will be described. FIG. 4 is a diagram schematically illustrating the configuration of the color filter 52 according to this embodiment. In the shown example, the color filter 52 includes color filters 52R transmitting only red light, color filters 52G transmitting only green light, color filters 52B transmitting only blue light, and color filters 52U transmitting only ultraviolet light.

The color filter 52R and the color filter 52U are alternately arranged in the odd lines of the color filter 52. The color filter 52G and the color filter 52B are alternately arranged in the even lines of the color filter 52. The imaging device 53 includes multiple pixels and one of the color filters 52R, 52G, 52B, and 52U is disposed in each pixel of the imaging device 53.

Accordingly, the pixel having the color filter 52R disposed therein photoelectrically converts red light out of light incident from the object to generate an image signal. The pixel having the color filter 52G disposed therein photoelectrically converts green light out of light incident from the object to generate an image signal. The pixel having the color filter 52B disposed therein photoelectrically converts blue light out of light incident from the object to generate an image signal. The pixel having the color filter 52U disposed therein photoelectrically converts ultraviolet light out of light incident from the object to generate an image signal.

Therefore, when the visible light LED 54 and the ultraviolet light LED 55 are applying light to the object, the imaging device 53 can generate image data based on an object image formed by the visible light and image data based on an object image formed by the ultraviolet light.

A method of generating inspection image data and measurement image data from the image data generated by the imaging device 53 will be described. The image data generated by the imaging device 53 is processed by the image signal processor 34 and is input to the image generating unit 41. The image generating unit 41 generates the inspection image data based on data corresponding to the pixels having the color filter 52R, the pixels having the color filter 52G, and the pixels having the color filters 52B among the input image data. The image generating unit 41 generates the measurement image data based on data corresponding to the pixels having the color filter 52U.

Figure 5:
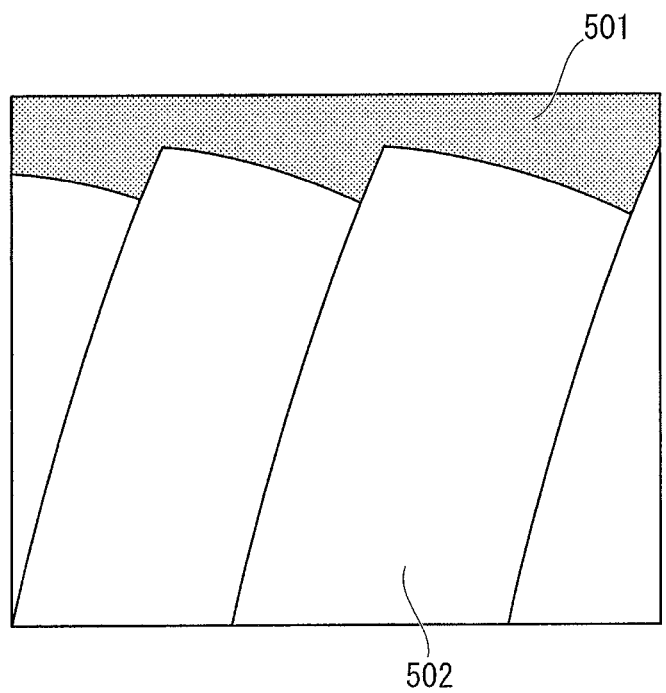
FIG. 5 is a diagram schematically illustrating an inspection image based on inspection image data generated by an image generating unit according to the first embodiment of the invention.

FIG. 5 is a diagram schematically illustrating an inspection image based on the inspection image data generated by the image generating unit 41 according to this embodiment. In the shown example, the inspection image includes a background 501 and a blade 502. When this image is captured, a striped pattern based on the ultraviolet light is projected to the blade 502 by the ultraviolet light LED 55 and the pattern filter 56. However, since the image generating unit 41 generates the inspection image data based on data corresponding to the pixels having the color filter 52R, the pixels having the color filter 52G, and the pixels having the color filter 52B, the inspection image data does not include the striped pattern based on the ultraviolet light. As viewed from the distal end portion 20, the background 501 corresponding to a part more distal than the blade 502 and the visible light emitted from the visible light LED 54 and the ultraviolet light emitted from the ultraviolet light LED 55 do not reach this part sufficiently.

Figure 6:
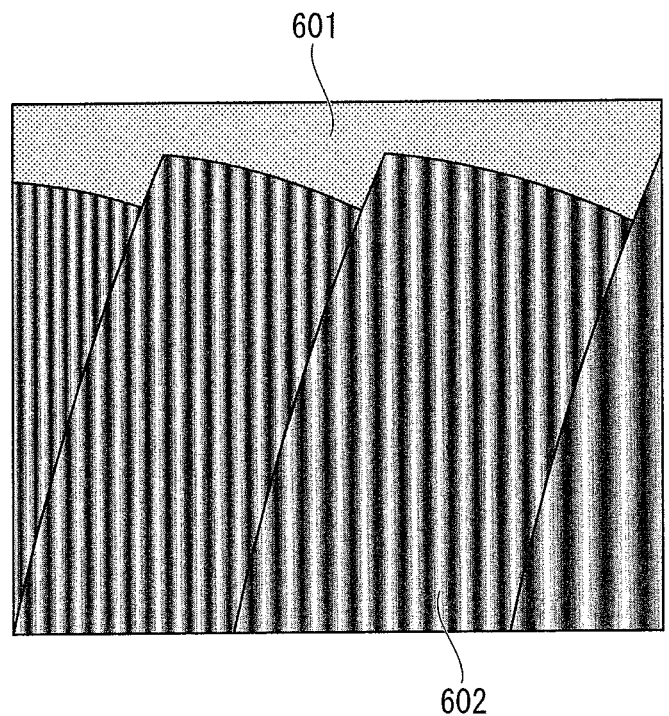
FIG. 6 is a diagram schematically illustrating a measurement image based on measurement image data generated by the image generating unit according to the first embodiment of the invention.

FIG. 6 is a diagram schematically illustrating the measurement image based on the measurement image data generated by the image generating unit 41 according to this embodiment. In the shown example, the measurement image includes a background 601 and a blade 602. When this image is captured, a striped pattern based on the ultraviolet light is projected to the blade 502 by the ultraviolet light LED 55 and the pattern filter 56. Since the image generating unit 41 generates the measurement image data based on data corresponding to the pixels having the color filter 52U, the measurement image data includes the striped pattern data.

Figure 7:
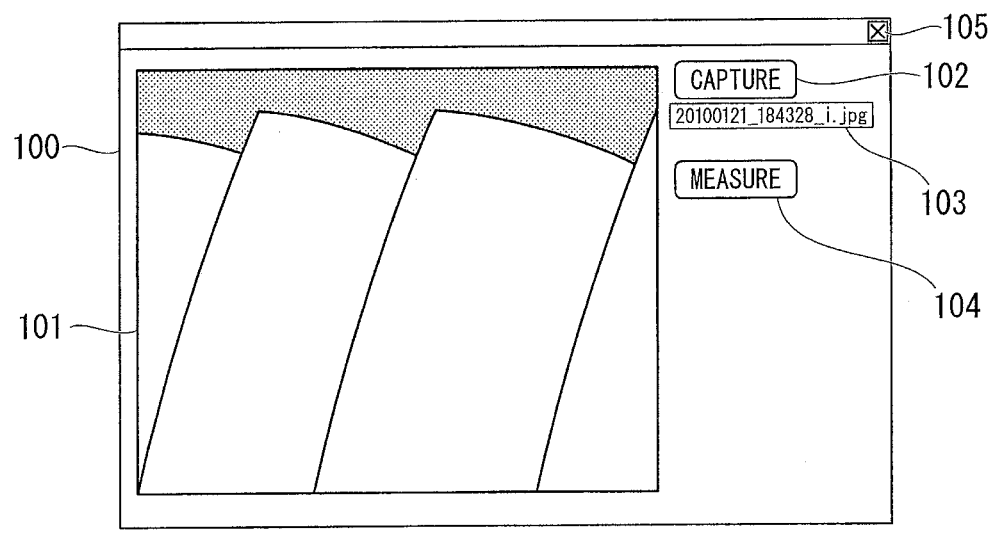
FIG. 7 is a diagram schematically illustrating a main window displayed on a monitor according to the first embodiment of the invention.

A display picture in this embodiment will be described. FIG. 7 shows a main window 100 displayed on the monitor 4 after the inspection apparatus 1 is started up. The main window 100 displays a live video box 101 displaying the inspection image, an image capture button 102 receiving an input instructing to capture an image, a file name box 103 displaying a file name of the captured inspection image data, a measurement button 104 receiving an input instructing to start the measurement, and an end button 105 receiving an input instructing to end the operation of the inspection apparatus 1.

FIG. 8 shows a measurement window 110 displayed on the monitor 4 when the inspection apparatus 1 starts a measurement process. In the shown example, the measurement window 110 includes an inspection image box 111 displaying an inspection image, a measurement image box 112 displaying a measurement image, a file name box 113 displaying a file name of the inspection image data, an image selection button 114 receiving an input instructing to select an inspection image, a file name box 115 displaying a file name of the measurement image data, an image switching button 116 receiving an input instructing to select a measurement image, a measurement result box 117 displaying the measurement result, and an end button 118 receiving an input instructing to end the measurement process. As shown in the drawing, the measurement window 110 displays the inspection image box 111 and the measurement image box 112 in parallel. The measurement window 110 displays a cursor 120 for designating a measurement point on the inspection image displayed on the inspection image box 112. A user can move the cursor 120 in the direction designated by direction keys by operating the direction keys of the operation unit 5. For example, when a downward direction is input by the use of the directional keys of the operation unit 5, the cursor 120 moves down.

The user can change the inspection image displayed on the inspection image box 111 by pressing the image selection button 114. The user can sequentially switch the measurement image displayed in the measurement image box 112 among three measurement images captured almost at the same time as the inspection image displayed in the inspection image box 111, by pressing the image switching button 116.

FIG. 9 shows the measurement window 110 displayed on the monitor 4 when the inspection apparatus 1 displays the result of the measurement process. The shown example is different from the measurement window 110 shown in FIG. 8, in that a mark 121 as a measurement point is displayed on the inspection image displayed in the inspection image box 112 and a mark 122 designating a position corresponding to the mark 121 is displayed on the measurement image displayed in the measurement image box 112. This means that an inspection image to be measured is selected and the measurement point is designated by the user.

The user can move the cursor 120 displayed on the inspection image by operating the direction keys of the operation unit 5 and designate the measurement point on the inspection image by pressing the measurement key of the operation unit 5. At this time, the mark 121 is displayed as a measurement point on the inspection image and the mark 122 is displayed as a point corresponding to the mark 121 on the measurement image. The measurement result of the designated measurement point is displayed in the measurement result box 117.

The measurement window 110 is a modal window, and the main window 100 cannot be operated while the measurement window 110 is being displayed on the monitor 4.

The flow of operations of the inspection apparatus 1 according to this embodiment will be described. FIG. 10 is a flowchart illustrating the flow of operations of the inspection apparatus 1 according to this embodiment.

(Step S11) The CPU 311 of the inspection apparatus 1 starts up software when a power supply is turned on. The CPU 311 serves as the main control unit 40, the image generating unit 41, the measurement position designating unit 42, the measurement processing unit 43, the graphic processing unit 44, and the matching unit 45 based on the started-up software. Thereafter, the process of step S12 is performed.

(Step S12) The main control unit 40 controls the imaging unit 201, the illumination control unit 33, the image signal processor 34, the image generating unit 41, and the graphic processing unit 44. Accordingly, the configurations start their operations and the main window 101 is displayed on the monitor 4. Thereafter, the process of step S13 is performed.

(Step S13) The main control unit 40 performs an initialization process. Thereafter, the process of step S14 is performed. The initialization process will be described later.

(Step S14) The main control unit 40 repeatedly performs a video display process, an image capturing process, and a measurement process until the end button 105 of the main window 100 is pressed. The video display process, the image capturing process, and the measurement process will be described later. When the end button 105 of the main window 100 is pressed, the process of step S15 is performed. The main control unit 40 performs the video display process and the image capturing process in synchronization with each other. Specifically, the main control unit 40 performs the video display process and the image capturing process again after both the video display process and the image capturing process are ended. The main control unit 40 repeatedly performs the measurement process without synchronization with other processes.

(Step S15) The main control unit 40 ends the process of displaying the main window 100 (the main window 100 is not displayed). Thereafter, the flow is ended.

The initialization process of step S13 in the flowchart shown in FIG. 10 will be described. FIG. 11 is a flowchart illustrating a flow of the initialization process in this embodiment.

(Step S101) The main control unit 40 stores an image capture counter Cs=0 in the RAM 313. The image capture counter Cs is a counter number of an image which is being image captured, and has values of 0 to 4. Thereafter, the process of step S102 is performed.

(Step S102) The main control unit 40 controls the illumination control unit 33 to change the striped pattern of the pattern filter 56 of the illumination unit 202 to "striped pattern 1". Thereafter, the process of step S103 is performed.

(Step S103) The main control unit 40 controls the illumination control unit 33 to turn on the visible light LED 54 and the ultraviolet light LED 55 of the illumination unit 202. Thereafter, the initialization process is ended.

Figure 12:
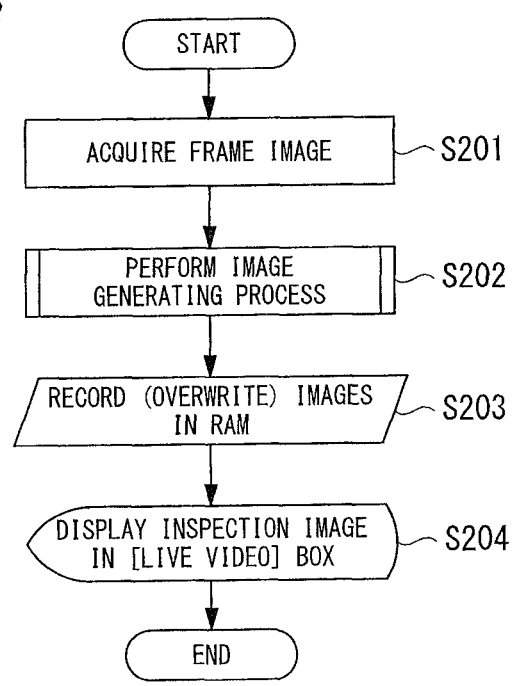
FIG. 12 is a flowchart illustrating a flow of a video display process according to the first embodiment of the invention.

The video display process of step S14 in the flowchart shown in FIG. 10 will be described. FIG. 12 is a flowchart illustrating the flow of the video display process in this embodiment.

(Step S201) The image generating unit 41 acquires frame image data (image data) generated by the image capturing of the imaging unit 201. The frame image data is image data corresponding to one frame acquired from the imaging device 53. Thereafter, the process of step S202 is performed.

(Step S202) The image generating unit 41 generates the inspection image data and the measurement image data from the image data acquired in step S201. Thereafter, the process of step S203 is performed. The process of generating the inspection image data and the measurement image data will be described later.

(Step S203) The main control unit 40 stores the inspection image data and the measurement image data generated by the image generating unit 41 in step S202 in the RAM 313. When the RAM 313 previously stores the inspection image data and the measurement image data, the inspection image data and the measurement image data newly generated in step S202 are overwritten on the data stored in the RAM 313. Thereafter, the process of step S204 is performed.

(Step S204) The image signal processor 34 displays an inspection image based on the inspection image data generated by the image generating unit 41 in step S202 in the live video box of the main window 100. Thereafter, the video display process is ended.

Figure 13:
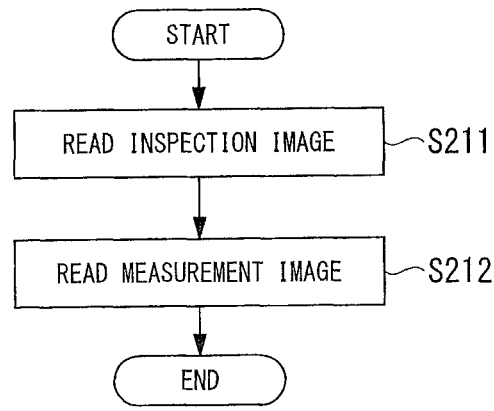
FIG. 13 is a flowchart illustrating a flow of processes of generating the inspection image data and the measurement image data according to the first embodiment of the invention.

The flow of processes of generating the inspection image data and the measurement image data in step S202 of the flowchart shown in FIG. 12 will be described. FIG. 13 is a flowchart illustrating the flow of the processes of generating the inspection image data and the measurement image data in this embodiment.

(Step S211) The image generating unit 41 generates the inspection image data based on the data corresponding to the pixels having the color filter 52R, the pixels having the color filter 52G, and the pixels having the color filter 52B out of the image data. Thereafter, the process of step S212 is performed.

(Step S212) The image generating unit 41 generates the measurement image data based on the data corresponding to the pixels having the color filter 52U out of the image data. Thereafter, the processes of generating the inspection image data and the measurement image data are ended.

Figure 14:
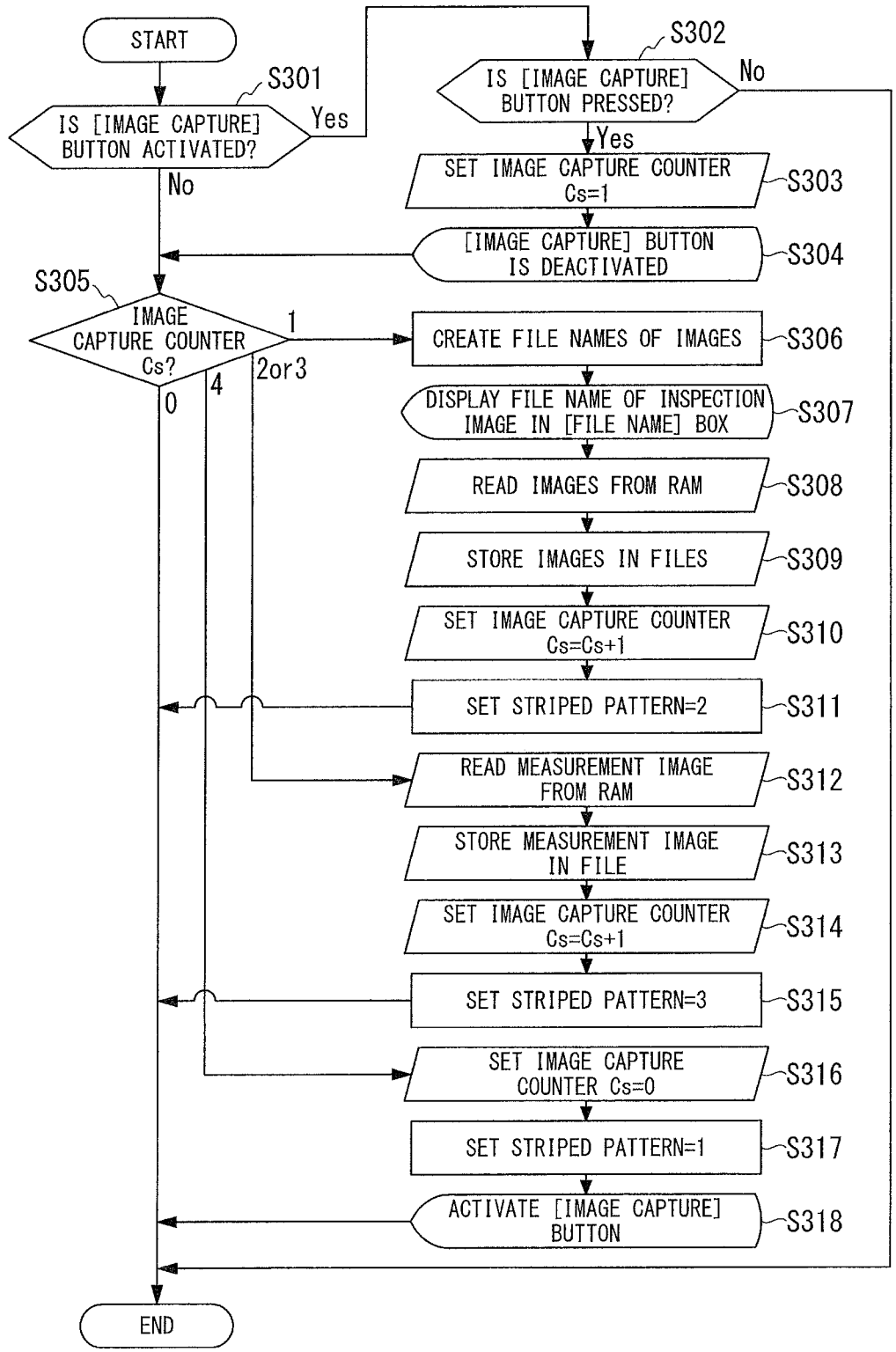
FIG. 14 is a flowchart illustrating a flow of an image capturing process according to the first embodiment of the invention.

The image capturing process of step S14 in the flowchart shown in FIG. 10 will be described. FIG. 14 is a flowchart illustrating the flow of the image capturing process in this embodiment.

(Step S301) The main control unit 40 determines whether the image capture button of the main window 100 is activated (in a pressing-possible state). When the main control unit 40 determines that the image capture button of the main window 100 is activated, the process of step S302 is performed. Otherwise, the process of step S305 is performed.

(Step S302) The main control unit 40 determines whether the image capture button of the main window 100 is pressed. When the main control unit 40 determines that the image capture button of the main window 100 is pressed, the process of step S303 is performed. Otherwise, the image capturing process is ended.

(Step S303) The main control unit 40 stores an image capture counter Cs=1 in the RAM 313. Thereafter, the process of step S304 is performed.

(Step S304) The main control unit 40 deactivates the image capture button of the main window 100 (a pressing-impossible state). Thereafter, the process of step S305 is performed.

(Step S305) The main control unit 40 reads the image capture counter Cs stored in the RAM 313. The main control unit 40 performs the process of step S306 when the read image capture counter Cs is "1", performs the process of step S312 when the image capture counter is "2" or "3", performs the process of step S316 when the image capture counter is "4", and ends the image capturing process when the image capture counter is "0".

(Step S306) The main control unit 40 generates the file name of the inspection image data and the file name of the measurement image data based on the date and time of creating the file names. Thereafter, the process of step S307 is performed. For example, it is assumed that the file name of the inspection image data is "creating date of the file name_creating time of the file name_i.jpg", and the file names of the measurement image data is "creating date of the file name_creating time of the file name_m1.jpg", "creating date of the file name_creating time of the file name_m2.jpg", and "creating date of the file name_creating time of the file name_m3.jpg". Specifically, when the creation date and time of the file name is "18:43:28 on January 21, 2010", the file name of the inspection image is "20100121_184328_i.jpg" and the file names of the measurement image data is "20100121_184328_m1.jpg", is "20100121_184328_m2.jpg", and is "20100121_184328_m3.jpg". "i" in the file name is a sign for identifying the inspection image data and "m" in the file names is a sign for identifying the measurement image data. In the file names of the measurement image data, the number after m represents the value of the image capture counter Cs at the time of storing the measurement image data.

(Step S307) The main control unit 40 displays the file name of the inspection image data generated in step S306 in the file name box 103 of the main window 100. Thereafter, the process of step S308 is performed.

(Step S308) The main control unit 40 reads the inspection image data and the measurement image data stored in the RAM 313. Thereafter, the process of step S309 is performed.

(Step S309) The main control unit 40 gives the file names generated in step S306 to the inspection image data and the measurement image data read in step S308 and stores the inspection image data and the measurement image data in the hard disk 317. Thereafter, the process of step S310 is performed. In step S309, since the image capture counter Cs is "1", the file name of the measurement image data is "creating date of the file name_creating time of the file name_m1.jpg".

(Step S310) The main control unit 40 adds "1" to the image capture counter Cs and stores the image capture counter Cs in the RAM 313. Thereafter, the process of step S311 is performed. Since the image capture counter Cs is "1" before the process of step S310, the image capture counter Cs is "2" after the process of step S310.

(Step S311) The main control unit 40 controls the illumination control unit 33 to change the striped pattern of the pattern filter 56 of the illumination unit 202 to "striped pattern 2". Thereafter, the image capturing process is ended.

(Step S312) The main control unit 40 reads the measurement image data stored in the RAM 313. Thereafter, the process of step S313 is performed.

(Step S313) The main control unit 40 gives the file name generated in step S306 to the measurement image data read in step S312 and stores the measurement image data in the hard disk 317. Thereafter, the process of step S314 is performed. In step S313, the image capture counter Cs is "2" or "3". Accordingly, when the image capture counter Cs is "2", the file name of the measured image data is "creating date of the file name_creating time of the file name_m2.jpg". When the image capture counter Cs is "3", the file name of the measurement image data is "creating date of the file name_creating time of the file name_m3.jpg".

(Step S314) The main control unit 40 adds "1" to the image capture counter Cs and stores the image capture counter Cs in the RAM 313. Thereafter, the process of step S315 is performed.

(Step S315) The main control unit 40 controls the illumination control unit 33 to change the striped pattern of the pattern filter 56 of the illumination unit 202 to "striped pattern 3". Thereafter, the image capturing process is ended.

(Step S316) The main control unit 40 stores the image capture counter Cs=0 in the RAM 313. Thereafter, the process of step 317 is performed.

(Step S317) The main control unit 40 controls the illumination control unit 33 to change the striped pattern of the pattern filter 56 of the illumination unit 202 to "striped pattern 1". Thereafter, the process of step S318 is performed.

(Step S318) The main control unit 40 activates the image capture button of the main window 100 (pressing-possible state). Thereafter, the image capturing process is ended.

Figure 15:
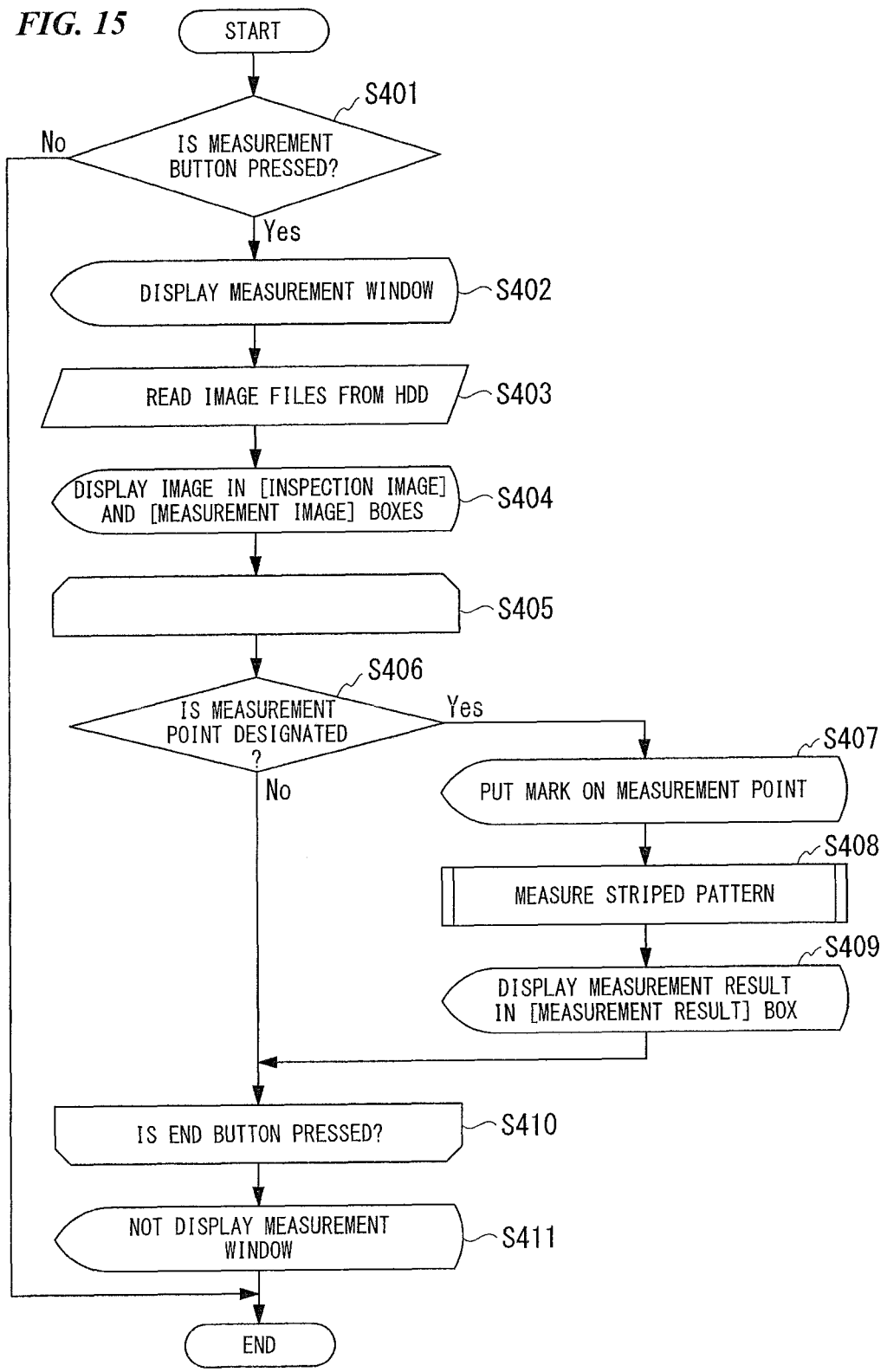
FIG. 15 is a flowchart illustrating a flow of a measurement process according to the first embodiment of the invention.

The measurement process of step S14 in the flowchart shown in FIG. 10 will be described. FIG. 15 is a flowchart illustrating the flow of the measurement process in this embodiment.

(Step S401) The main control unit 40 determines whether the measurement button of the main window 100 is pressed. When the main control unit 40 determines that the measurement button of the main window 100 is pressed, the process of step S402 is performed. Otherwise, the measurement process is ended.

(Step S402) The main control unit 40 controls the image signal processor 34, the image generating unit 41, and the graphic processing unit 44 to display the measurement window 110 on the monitor 4. The main control unit 40 deactivates the main window 100 (operation-impossible state). Thereafter, the process of step S403 is performed.

(Step S403) User holds an image selection button 114 of a measurement window 110 down and selects inspection image data in which a measurement object is picked up. The main control unit 40 reads the file having the newest date of the file name out of the files of the inspection image data stored in the hard disk 317. Then, the main control unit 40 reads three measurement image data having the same date and time in the file names of the read inspection image data. Thereafter, the process of step S404 is performed.

(Step S404) The main control unit 40 displays the inspection image based on the inspection image data read in step S403 in the inspection image box 111 of the measurement window 110. The main control unit 40 displays the measurement image based on the "creating date of the file name_creating time of the file name_m1.jpg" out of the three measurement image data read in step S403 in the measured image box 112 of the measurement window 110. Thereafter, the process of step S405 is performed.

(Step S405) The processes of steps S405 to S410 are repeatedly performed until the end button 118 of the measurement window 110 is pressed. When the end button 118 of the measurement window 110 is pressed, the repeated processes of steps S405 to S410 are ended and the process of step S411 is performed.

(Step S406) A user operates the direction keys of the operation unit 5 at the time of making a measurement to move the cursor 120 on the measurement image displayed in the measurement image box 111 of the measurement window 110 and to select the position to be measured. By causing the user to press the measurement key of the operation unit 5, the main control unit 40 determines whether the position to be measured is designated by the user. When the main control unit 40 determines that the position to be measured is designated by the user, the process of step S407 is performed. Otherwise, the process of step S410 is performed.

(Step S407) The measurement position designating unit 42 designates the position to be measured in the observed image based on the input from the operation unit 5 in step S406. Subsequently, the matching unit 45 designates the position in the measurement image corresponding to the position designated by the measurement position designating unit 42. Subsequently, the graphic processing unit 44 puts the marks 121 and 122 at the position designated by the measurement position designating unit 42 in the inspection image and the position in the measurement image. Thereafter, the process of step S408 is performed.

(Step S408) The measurement processing unit 43 measures an object at the position designated by the matching unit 45 in step S407 using a phase shift method based on the three measurement images read in step S403. Accordingly, the measurement processing unit 43 can calculate three-dimensional coordinates of the position designated by the matching unit 45 in step S407. Thereafter, the process of step S409 is performed.

(Step S409) The main control unit 40 displays the measurement result by the measurement processing unit 43 in step S408 in the measurement result box 117 of the measurement window 110. Thereafter, the process of step S410 is performed.

(Step S410) The main control unit 40 determines whether the end button 118 of the measurement window 110 is pressed. When the main control unit 40 determines that the end button 118 of the measurement window 110 is pressed, the process of step S411 is performed. Otherwise, the process of step S405 is performed again.

(Step S411) The main control unit 40 ends the process of displaying the measurement window 110 (the measurement window 110 is not displayed). The main control unit 40 activates the main window 100 (operation-possible state). Thereafter, the measurement process is ended.

According to the above-mentioned configurations and processes, the inspection apparatus 1 can acquire the inspection image data and the measurement image data without switching the turning-on and turning-off of the visible light LED 54 for observing an object and the turning-on and turning-off of the ultraviolet light LED 55 for projecting the striped pattern to the object. Accordingly, the operation for acquiring the inspection image data and the operation for acquiring the measurement image data can be more simplified and facilitated. The inspection apparatus 1 can display the inspection image and the measurement image captured at the same time in parallel. Accordingly, the user can designate the measurement point with reference to the inspection image to which the striped pattern is not projected and can easily determine at what position the measurement point is designated.

In the above-mentioned example, the color filter 52 includes the color filters 52R transmitting only red light, the color filters 52G transmitting only green light, and the color filters 52B transmitting only blue light, but it is not limited to this configuration. For example, at the time of acquiring a monochromatic inspection image, a filter transmitting only visible light and a filter transmitting only ultraviolet light may be used instead of the RGB color filters.

Figure 16:
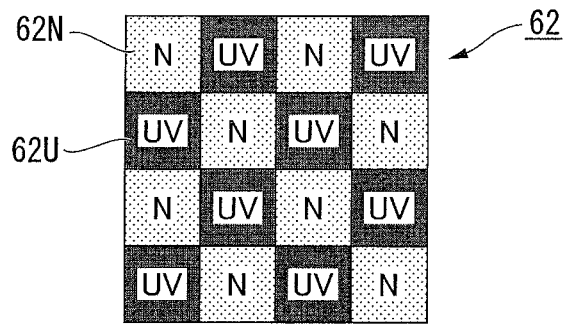
FIG. 16 is a diagram schematically illustrating the arrangement of color filters used for capturing a monochromic inspection image according to the first embodiment of the invention.

FIG. 16 is a diagram schematically illustrating the configuration of a color filter 62 used to capture of a monochromatic inspection image in this embodiment. In the shown example, the color filter 62 includes color filters 62N transmitting only visible light and color filters 62U transmitting ultraviolet light.

The color filters 62N and the color filters 62U are alternately arranged in the color filter 62. One of the color filters 62N and 52U is disposed in each pixel of the imaging device 53.

Accordingly, the pixels having the color filter 62N disposed therein photoelectrically converts visible light incident from an object to generate an image signal. The pixels having the color filter 62U disposed therein photoelectrically converts ultraviolet light out of the light incident from the object to generate an image signal.

Therefore, when the visible light LED 54 and the ultraviolet light LED 55 are applying light to the object, the imaging device 53 can generate image data including the monochromatic inspection image data based on the object image formed by the visible light and the measurement image data based on the object image formed by the ultraviolet light.

Second Embodiment

A second embodiment of the invention will be described below. In this embodiment, a striped pattern is projected to an object using a visible light LED instead of the ultraviolet light LED in the first embodiment. The inspection apparatus 10 according to this embodiment is different from the inspection apparatus 1 according to the first embodiment, in the configuration of a distal end portion 70. The other configurations of the inspection apparatus 10 are the same as the configurations of the inspection apparatus 1 according to the first embodiment.

Figure 17:
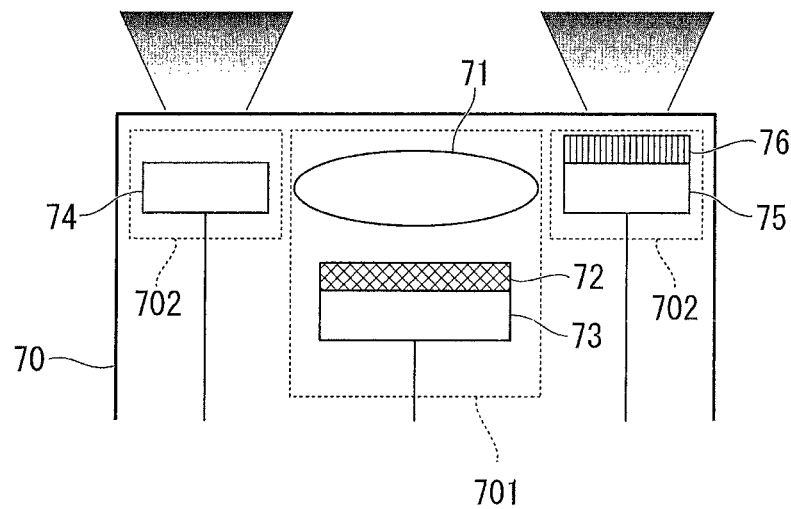
FIG. 17 is a diagram schematically illustrating the configuration of a distal end portion according to a second embodiment of the invention.

The configuration of the distal end portion 70 will be described. FIG. 17 is a diagram schematically illustrating the configuration of the distal end portion 70 in this embodiment. In the shown example, an imaging unit 701 and a illumination unit 702 are disposed in the distal end portion 70. The imaging unit 701 includes an imaging optical system 71, a color filter 72, and an imaging device 73. The color filter 72 is disposed on the light-receiving surface of the imaging device 73. The imaging optical system 71 forms an object image on the light-receiving surface of the imaging device 73. The color filter 72 is a Bayer array color filter. The imaging device 73 photoelectrically converts the object image formed through the imaging optical system 71 and the color filter 72 to generate an image signal.

The illumination unit 702 includes visible light LEDs 74 and 75 and a pattern filter 76. The visible light LEDs 74 and 75 emit visible light applied to the object. The pattern filter 76 is a filter blocking the visible light emitted from the visible light LED 75 in a striped shape, and is disposed on the visible light emitting surface of the visible light LED 75. Accordingly, the visible light emitted from the visible light LED 75 passes through the pattern filter 76 and projects a striped pattern to the object.

The pattern filter 76 is the same as the pattern filter 56 in the first embodiment. Accordingly, when the visible light LEDs 74 and 75 are applying light to the object, the imaging device 73 can generate image data of the object to which the striped pattern is projected.

The flow of operations of the inspection apparatus 10 according to this embodiment will be described. The flow of operations of the inspection apparatus 10 according to this embodiment is different from the flow of operations of the inspection apparatus 1 according to the first embodiment, in the flow of processes of generating inspection image data and the measurement image data. The other processes performed by the inspection apparatus 10 are the same as the other processes performed by the inspection apparatus 1 according to the first embodiment.

Figure 18:
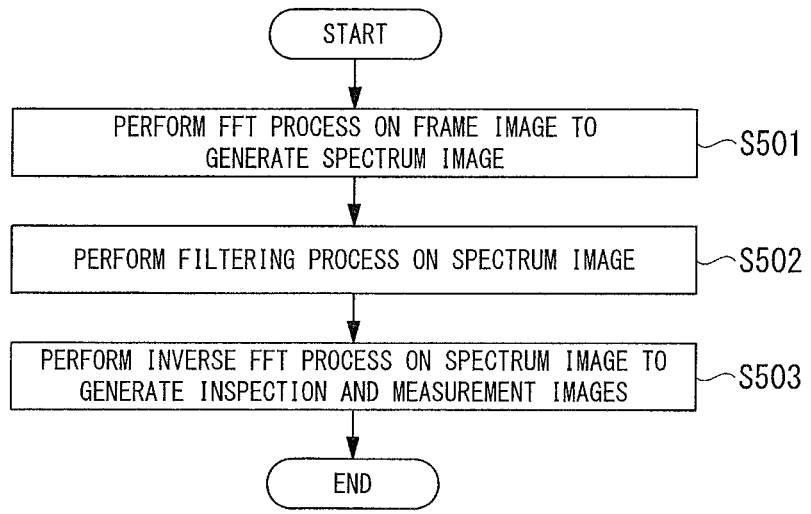
FIG. 18 is a flowchart illustrating a flow of processes of generating the inspection image data and the measurement image data according to the second embodiment of the invention.

The flow of processes of generating the inspection image data and the measurement image data in this embodiment will be described. FIG. 18 is a flowchart illustrating the flow of processes of the inspection image data and the measurement image data in this embodiment.

(Step S501) The image generating unit 41 performs an FFT (Fast Fourier Transform) process on image data to generate a spectrum image. Thereafter, the process of step S502 is performed.

(Step S502) The image generating unit 41 applies a band removal filter (spatial frequency filter) removing a striped spectrum to the spectrum image generated in step S501 to generate a first spectrum image including a spectrum corresponding to the shape of a blade 702. The image generating unit 41 applies a band transmission filter (spatial frequency filter) transmitting a striped spectrum to the spectrum image generated in step S501 to generate a second spectrum image including a spectrum corresponding to the striped pattern. Thereafter, the process of step S503 is performed.

(Step S503) The image generating unit 41 performs an inverse FFT process on the first spectrum image including the spectrum corresponding to the shape of the blade 702 and being generated in step S502 to generate an inspection image. The image generating unit 41 performs the inverse FFT process on the second spectrum image including the spectrum corresponding to the striped pattern and being generated in step S502 to generate a measurement image. Thereafter, the process of generating the inspection image data and the measurement image data is ended.

The filter used in the processes of steps S501 to S503 and the images generated in the processes will be described.

Figure 19:
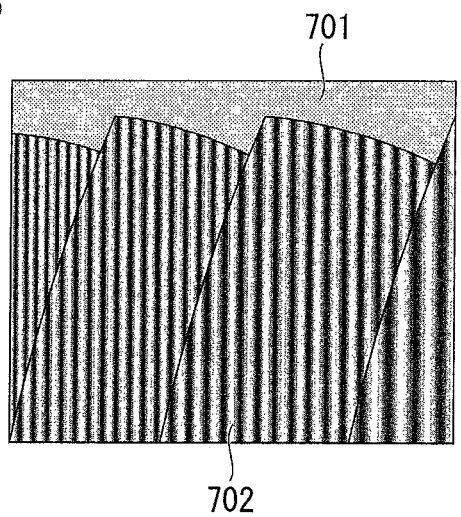
FIG. 19 is a diagram schematically illustrating an image based on image data generated by an imaging device according to the second embodiment of the invention.

FIG. 19 is a diagram schematically illustrating an image based on the image data generated by the imaging device 73 according to this embodiment. In the shown example, the image includes a background 701 and a blade 702. When this image is captured, the striped pattern based on the visible light is projected to the blade 702 by the visible light LED 75 and the pattern filter 76.

Figure 20:
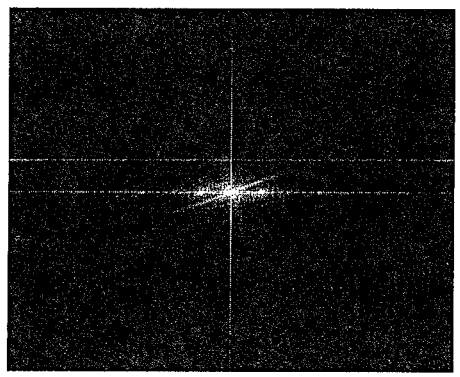
FIG. 20 is a diagram schematically illustrating a spectrum image generated by an image generating unit according to the second embodiment of the invention.

FIG. 20 is a diagram schematically illustrating the spectrum image generated by the image generating unit 41 in this embodiment. In the shown example, a spectrum in the horizontal direction corresponding to the striped pattern and spectrums in the vertical direction and an oblique direction corresponding to the shape of the blade 702 are shown.

Figure 21:
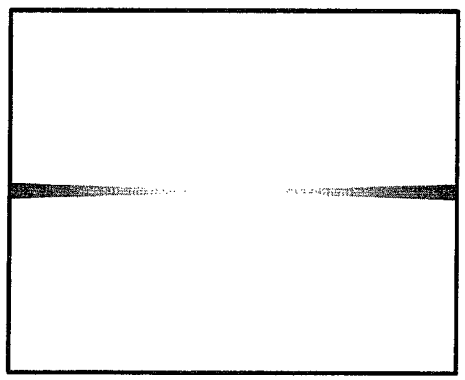
FIG. 21 is a diagram schematically illustrating a band removal filter removing a striped spectrum according to the second embodiment of the invention.

FIG. 21 is a diagram schematically illustrating the band removal filter removing the striped spectrum in this embodiment. In the shown example, the white part transmits the spectrum the black part removes the spectrum. In this embodiment, since the image data generated by the imaging device 73 includes a striped pattern having a predetermined spatial frequency in the horizontal direction, the band removal filter removing the striped spectrum is a filter which can remove only specific spatial frequency component in the horizontal direction.

Figure 22:
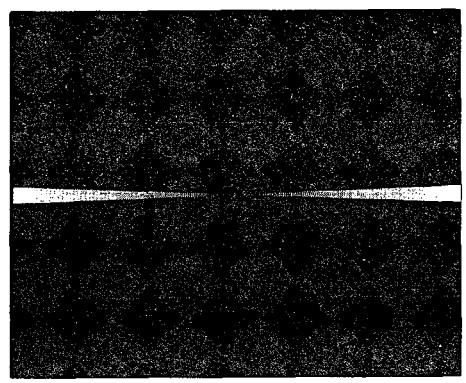
FIG. 22 is a diagram schematically illustrating a band transmission filter transmitting a striped spectrum according to the second embodiment of the invention.

FIG. 22 is a diagram schematically illustrating the band transmission filter transmitting the striped pattern in this embodiment. In the shown example, the white part transmits a spectrum and the black part removes the spectrum. In this embodiment, since the image data generated by the imaging device 73 includes a striped pattern having a predetermined spatial frequency in the horizontal direction, the band transmission filter transmitting a striped spectrum is a filter transmitting only a specific spatial frequency component in the horizontal direction.

Figure 23:
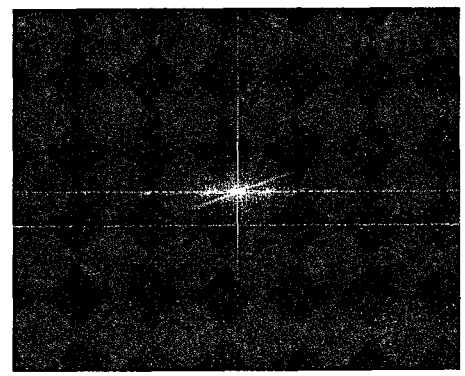
FIG. 23 is a diagram schematically illustrating a first spectrum image including a spectrum corresponding to a blade shape according to the second embodiment of the invention.

FIG. 23 is a diagram schematically illustrating the first spectrum image including the spectrum corresponding to the shape of the blade 702 in this embodiment. In the shown example, the spectrum corresponding to the striped pattern is removed from the spectrum image shown in FIG. 20.

Figure 24:
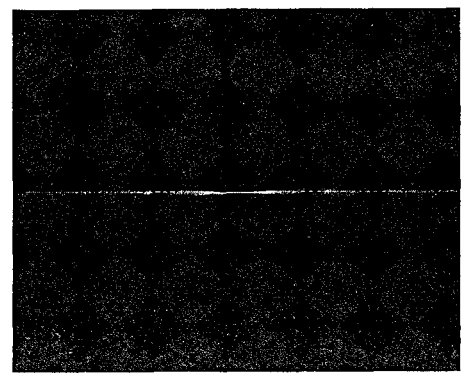
FIG. 24 is a diagram schematically illustrating a second spectrum image including a spectrum corresponding to a striped pattern according to the second embodiment of the invention.

FIG. 24 is a diagram schematically illustrating the second spectrum image including the spectrum corresponding to the striped pattern in this embodiment. In the shown example, the spectrum corresponding to the blade 702 is removed from the spectrum image shown in FIG. 20.

Figure 25:
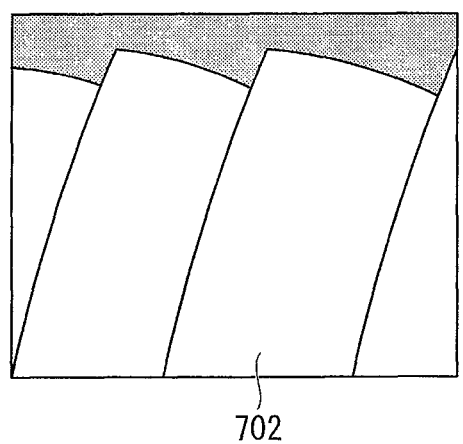
FIG. 25 is a diagram schematically illustrating an inspection image generated by the image generating unit according to the second embodiment of the invention.

FIG. 25 is a diagram schematically illustrating the inspection image generated by the image generating unit 41 in this embodiment. In the shown example, the blade 702 from which the striped pattern is removed is shown.

Figure 26:
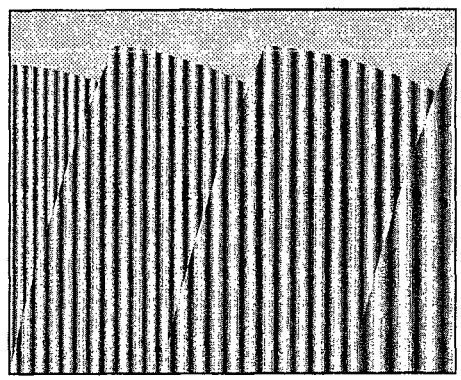
FIG. 26 is a diagram schematically illustrating a measurement image generated by the image generating unit according to the second embodiment of the invention.

FIG. 26 is a diagram schematically illustrating the measurement image generated by the image generating unit 41 in this embodiment. In the shown example, the striped pattern is shown.

According to the above-mentioned configurations and processes, the inspection apparatus 10 can acquire the inspection image data and the measurement image data without switching the turning-on and turning off of the visible light LED 74 for observing an object and the turning-on and turning-off of the visible light LED 75 for projecting the striped pattern to the object. Accordingly, the operation for acquiring the inspection image data and the operation for acquiring the measurement image data can be more simplified and facilitated. The inspection apparatus 10 can display the inspection image and the measurement image captured at the same time in parallel. Accordingly, the user can designate the measurement point with reference to the inspection image to which the striped pattern is not projected and can easily determine at what position the measurement point is designated.

Third Embodiment

A third embodiment of the invention will be described. The inspection apparatus 11 according to this embodiment includes multiple ultraviolet light LEDs and thus acquires multiple measurement images at a time, unlike the inspection apparatus 1 according to the first embodiment. The inspection apparatus 11 according to this embodiment is different from the inspection apparatus 1 according to the first embodiment, in the configuration of a distal end portion 80. The other configurations of the inspection apparatus 11 are the same as the other configurations of the inspection apparatus 1 according to the first embodiment.

Figure 27:
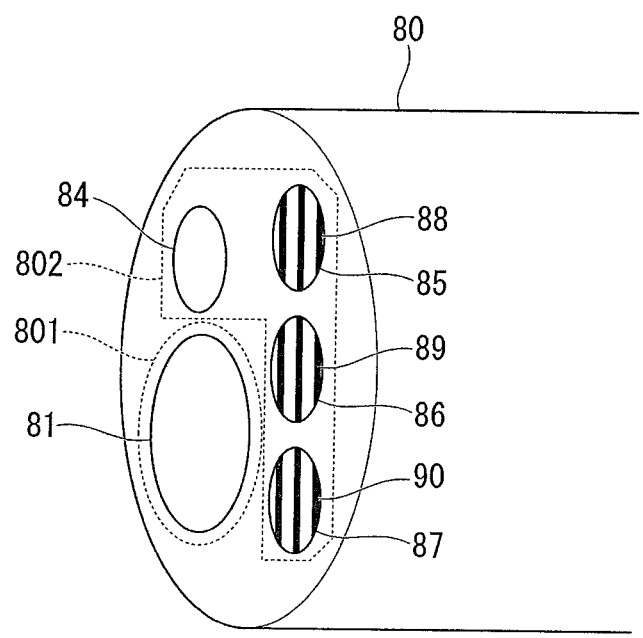
FIG. 27 is a diagram schematically illustrating an appearance of a distal end portion according to a third embodiment of the invention.

The configuration of the distal end portion 80 will be described. FIG. 27 is a diagram schematically illustrating the appearance of the distal end portion 80 in this embodiment. In the shown example, the distal end portion 80 includes an imaging unit 801 and a illumination unit 802. The imaging unit 801 includes an imaging optical system 81, a color filter 82 (not shown), and an imaging device 83 (not shown), similarly to the first embodiment.

The illumination unit 802 includes a visible light LED 84, ultraviolet light LEDs 85 to 87, and pattern filters 88 to 90. The visible light LED 84 emits visible light to be applied to an object. The ultraviolet light LED 85 emits ultraviolet light of a first wavelength to be applied to the object. The ultraviolet light LED 86 emits ultraviolet light of a second wavelength to be applied to the object. The ultraviolet light LED 87 emits ultraviolet light of a third wavelength to be applied to the object. The first to third wavelengths are different from each other. The pattern filters 88 to 90 are filters blocking the ultraviolet light emitted from the ultraviolet light lamps 85 to 87 in a striped shape and are disposed on the ultraviolet light-emitting surfaces of the ultraviolet light lamps 85 to 87, respectively. Accordingly, the ultraviolet light of the first wavelength emitted from the ultraviolet light LED 85 passes through the pattern filter 88 and projects a striped pattern to the object. The ultraviolet light of the second wavelength emitted from the ultraviolet light LED 86 passes through the pattern filter 89 and projects a striped pattern onto the object. The ultraviolet light of the third wavelength emitted from the ultraviolet light LED 87 passes through the pattern filter 90 and projects a striped pattern onto the object.

The striped patterns of the pattern filters 88 to 90 are striped patterns "1" to "3" having different phases. Striped patterns "1" to "3" partially block the ultraviolet light emitted from the ultraviolet light LEDs 85 to 87 and include plural linear patterns having different phases. The pattern filters 88 to 90 are disposed in the distal end portion 80 so that the striped patterns of the filters are parallel to each other.

Accordingly, the illumination unit 802 can project the plural striped patterns having different phases onto the object at a time.

Figure 28:
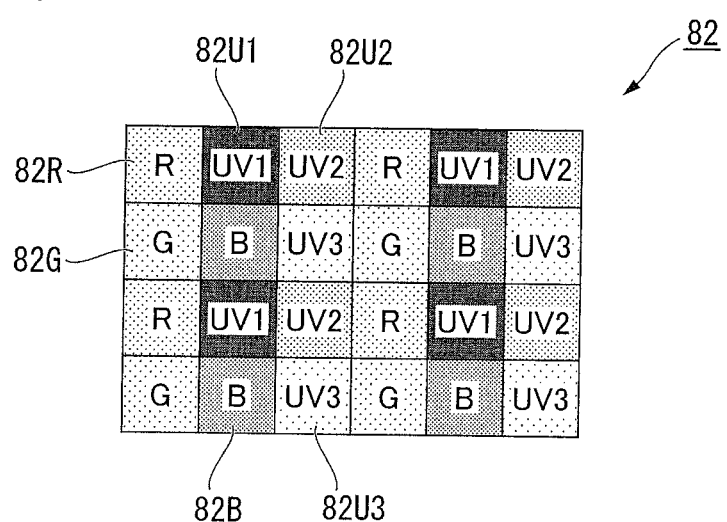
FIG. 28 is a diagram schematically illustrating an arrangement of color filters according to the third embodiment of the invention.

The configuration of the color filter 82 will be described. FIG. 28 is a diagram schematically illustrating the configuration of the color filter 82 in this embodiment. In the shown example, the color filter 82 includes a color filter 82R transmitting only red light, a color filter 82G transmitting only green light, a color filter 82B transmitting only blue light, a color filter 82U1 transmitting only ultraviolet light of the first wavelength, a color filter 82U2 transmitting only ultraviolet light of the second wavelength, and a color filter 82U3 transmitting only ultraviolet light of the third wavelength.

The color filter 82R, the color filter 82U1, and the color filter 82U2 are sequentially arranged in the odd lines of the color filter 82. The color filter 82G, the color filter 82B, and the color filter 82U3 are sequentially arranged in the even lines of the color filter 82. The imaging device 83 includes multiple pixels. One of the color filters 82R, 82Q 82B, 82U1, 82U2, and 82U3 is disposed in each pixel of the imaging device 83.

Accordingly, the pixels having the color filter 82R disposed therein photoelectrically converts red light out of the light incident from the object to generate an image signal. The pixels having the color filter 82G disposed therein photoelectrically converts green light out of the light incident from the object to generate an image signal. The pixels having the color filter 82B disposed therein photoelectrically converts blue light out of the light incident from the object to generate an image signal. The pixels having the color filter 82U1 disposed therein photoelectrically converts ultraviolet light of the first wavelength out of the light incident from the object to generate an image signal. The pixels having the color filter 82U2 disposed therein photoelectrically converts ultraviolet light of the second wavelength out of the light incident from the object to generate an image signal. The pixels having the color filter 82U3 disposed therein photoelectrically converts ultraviolet light of the third wavelength out of the light incident from the object to generate an image signal.

Therefore, when the visible light LED 84 and the ultraviolet light LEDs 85 to 87 are applying light to the object, the imaging device 83 can generate image data including image data based on the object image formed by the visible light, image data based on the object image formed by the ultraviolet light of the first wavelength, image data based on the object image formed by the ultraviolet light of the second wavelength, and image data based on the object image formed by the ultraviolet light of the third wavelength.

A method of generating the inspection image data and the measurement image data from the image data generated by the imaging device 83 will be described. The image data generated by the imaging device 83 are processed by the image signal processor 34 and input to the image generating unit 41. The image generating unit 41 generates the inspection image data based on data corresponding to the pixels having the color filter 82R, the pixels having the color filter 82G, and the pixels having the color filter 82B out of the input image data. The image generating unit 41 generates first measurement image data based on data corresponding to the pixels having the color filter 82U1, generates second measurement image data based on data corresponding to the pixels having the color filter 82U2, and generates third measurement image data based on data corresponding to the pixels having the color filter 82U3.

Accordingly, the inspection apparatus 11 can acquire the inspection image data and plural measurement image data at the same time.

When multiple measurement images are sequentially captured, the angles of the object shown in the measurement images are different with the movement of the object or the distal end portion 80 during the capturing of the measurement images. Accordingly, these measurement images are not appropriate for the measurement. However, in this embodiment, since multiple measurement images are captured at a time, the angles of the object shown in the measurement images are equal to each other. Accordingly, it is possible to acquire multiple measurement images more appropriate for the measurement.

The measurement method according to this embodiment is the same as the measurement method according to the first embodiment.

According to the above-mentioned configurations and processes, the inspection apparatus 11 can acquire inspection image data and multiple measurement image data without switching the striped pattern of the pattern filter for projecting the striped pattern to the object. Accordingly, the operation for acquiring the inspection image data and the operation for acquiring the measurement image data can be more simplified and facilitated.

Although exemplary embodiments of the invention have been described, the invention is not limited to the embodiments. The configurations can be added, removed, replaced, and modified without departing from the spirit and scope of the invention. The invention is not limited to the above description, but is limited only by the appended claims.

For example, although "striped pattern 1" to "striped pattern 3" have been exemplified as the striped pattern of the pattern filter in the above-mentioned embodiments, the invention is not limited to this configuration, but four or more types of striped patterns may be used.

The above-mentioned processes may be performed by recording a program for measuring an object based on images captured by the inspection apparatus in a computer-readable recording medium and causing a computer system to read and execute the program recorded in the recording medium. Here, the "computer system" may include an OS or hardware such as peripherals.

The "computer system" may include a home page providing environment (or display environment), when it uses a WWW system.

The "computer-readable recording medium" may be writable nonvolatile memories such as a flexible disk, a magneto-optical disk, a ROM, and a flash memory, portable mediums such as a DVD (Digital Versatile Disk), memory devices such as a hard disk built in the computer system.

The "computer-readable recording medium" may include mediums temporarily storing programs, such as volatile memories (for example, DRAM (Dynamic Random Access Memory) in the computer system serving as a server or a client when the program is transmitted via a network such as the Internet or a communication circuit such as a telephone line.

The program may be transmitted from a computer system storing the program in its memory device via a transmission medium or via transmission waves in the transmission medium to another computer system. Here, the "transmission medium" transmitting the program means a medium having a function of transmitting information, like a network (communication network) such as the Internet or a communication circuit (communication line) such as a telephone line.

The program may implement a part of the above-mentioned functions. The program may be a program which can perform the above-mentioned functions by combination with a program previously recorded in the computer system, that is, a so-called difference file (difference program).

What is claimed is:

1. An inspection apparatus comprising:
    an insertion portion which is inserted into a device under inspection;
    a projection unit which projects light which forms a striped pattern onto an object inside the device, the striped pattern includes a plurality of linear patterns used to measure the object by a phase shift method;
    an imaging unit which is provided in the insertion portion and images the object onto which the striped pattern is projected and generates image data;
    a generation unit which generates first image data forming a first image not including the striped pattern and second image data forming a second image including the striped pattern from the image data generated by the imaging unit;
    a designation unit which designates a position in the first image based on an instruction input through an input device;
    a display unit which displays the first image and the second image and displays a mark at the position in the first image designated by the designation unit; and
    a measurement unit which measures the object using the second image data with the phase shift method based on the position indicated by the mark,
    wherein the projection unit comprises a first projection unit which projects observation light onto the object and a second projection unit which projects light which forms the striped pattern onto the object,
    wherein the observation light is in a first wavelength band and the light which forms the striped pattern is in a second wavelength band other than the first wavelength band, wherein the imaging unit comprises an imaging device having a plurality of pixels, a first one of the plurality of pixels converting the observation light into a first signal and a second one of the plurality of pixels converting the light which forms the striped pattern into a second signal, and wherein the generation unit generates the first image data based on the first signal and generates the second image data based on the second signal.

2. The inspection apparatus according to claim 1, wherein the light in the first wavelength band is visible light, and wherein the light in the second wavelength band is ultraviolet light.

3. The inspection apparatus according to claim 2, wherein the first pixel comprises a visible light filter transmitting only visible light and the second pixel comprises an UV filter transmitting only ultraviolet light.

4. The inspection apparatus according to claim 2, wherein four pixels are disposed as a basic unit in the imaging device of the imaging unit, and
    wherein the basic unit includes the first pixel having a color filter transmitting only red light, the third pixel having a color filter transmitting only green light, the fourth pixel having a color filter transmitting only blue light, and the second pixel having an UV filter transmitting only ultraviolet light.

5. The inspection apparatus according to claim 1, wherein the display unit displays a mark at a position in the second image corresponding to the position in the first image designated by the designation unit.

6. A measurement method of an inspection apparatus including an imaging device having a plurality of pixels, the method comprising:
    projecting observation light onto an object and projecting light which forms a striped pattern onto the object, the striped pattern includes a plurality of linear patterns to measure the object by a phase shift method, the observation light being in a first wavelength band and the light which forms the striped pattern being in a second wavelength band other than the first wavelength band;
    imaging the object onto which the striped pattern is projected and generating image data;
    converting, with a first one of the plurality of pixels, the observation light into a first signal and converting, with a second one of the plurality of pixels, the light which forms the striped pattern into a second signal;
    generating first image data forming a first image not including the striped pattern and second image data forming a second image including the striped pattern from the image data generated by the imaging unit, generating the first image data being based on the first signal and generating the second image data being based on the second signal;
    designating a position in the first image based on an instruction input through an input device;
    displaying the first image and the second image and displaying a mark at the position in the first image designated in the designating; and
    measuring the object using the second image data with the phase shift method based on the position indicated by the mark.

* * * * *